(12) United States Patent
Abe

(10) Patent No.: US 7,758,496 B2
(45) Date of Patent: Jul. 20, 2010

(54) DIAGNOSTIC SYSTEM USING ENDOSCOPE

(75) Inventor: Kazunori Abe, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 965 days.

(21) Appl. No.: 11/528,640

(22) Filed: Sep. 28, 2006

(65) Prior Publication Data

US 2007/0078303 A1 Apr. 5, 2007

(30) Foreign Application Priority Data

Sep. 30, 2005 (JP) .............................. 2005-288359

(51) Int. Cl.
*A61B 1/00* (2006.01)
(52) U.S. Cl. ..................... 600/118; 600/109; 600/101
(58) Field of Classification Search ................. 600/101, 600/109, 118; 370/277
See application file for complete search history.

(56) References Cited

U.S. PATENT DOCUMENTS

| | | | | |
|---|---|---|---|---|
| 4,821,097 | A * | 4/1989 | Robbins | 348/485 |
| 6,955,671 | B2 * | 10/2005 | Uchikubo | 606/1 |
| 7,158,860 | B2 * | 1/2007 | Wang et al. | 700/245 |
| 7,222,000 | B2 * | 5/2007 | Wang et al. | 700/259 |
| 7,386,730 | B2 * | 6/2008 | Uchikubo | 713/182 |
| 7,485,115 | B2 * | 2/2009 | Nakamura | 606/1 |
| 2002/0147384 | A1 * | 10/2002 | Uchikubo | 600/109 |
| 2003/0097042 | A1 * | 5/2003 | Eino | 600/118 |
| 2004/0230094 | A1 * | 11/2004 | Nakamura | 600/101 |
| 2005/0240631 | A1 * | 10/2005 | Willard et al. | 707/200 |
| 2005/0283047 | A1 * | 12/2005 | Tashiro et al. | 600/118 |
| 2006/0062331 | A1 * | 3/2006 | Shirazi et al. | 375/326 |

FOREIGN PATENT DOCUMENTS

JP 2000-271147 A 10/2000
JP 2005-111080 A 4/2005

OTHER PUBLICATIONS

Rosser et al., Surgical Endoscopy, vol. 11, No. 8, pp. 858-855, (Aug. 1997) XP002412900.
Varkarakis et al., Urology, vol. 65, No. 5, pp. 840-846, (May 2005) XP004881874.

* cited by examiner

*Primary Examiner*—John P Leubecker
(74) *Attorney, Agent, or Firm*—Birch, Stewart, Kolasch & Birch, LLP

(57) ABSTRACT

In a diagnostic system, a diagnostic unit for an operator of an electronic endoscope and a diagnostic unit for an instructor are in half-duplex radio communication. An inquiry that is input as a voice signal through a microphone into the electronic endoscope is superimposed on a modulated picture signal while shifting the phase of the voice signal, to produce an RF signal, which is sent as an electric wave to an operator's processor and an instructor's processor. The processors demodulate the RF signal, to display an endoscopic image based on the picture signal and output the inquiry through speakers based on the voice signal. An instruction that is input as a voice signal through a microphone into the instructor's processor is superimposed on a dummy signal, to produce an RF signal, which is sent as an electric wave to the operator's processor, to output the instruction through the speaker.

6 Claims, 7 Drawing Sheets

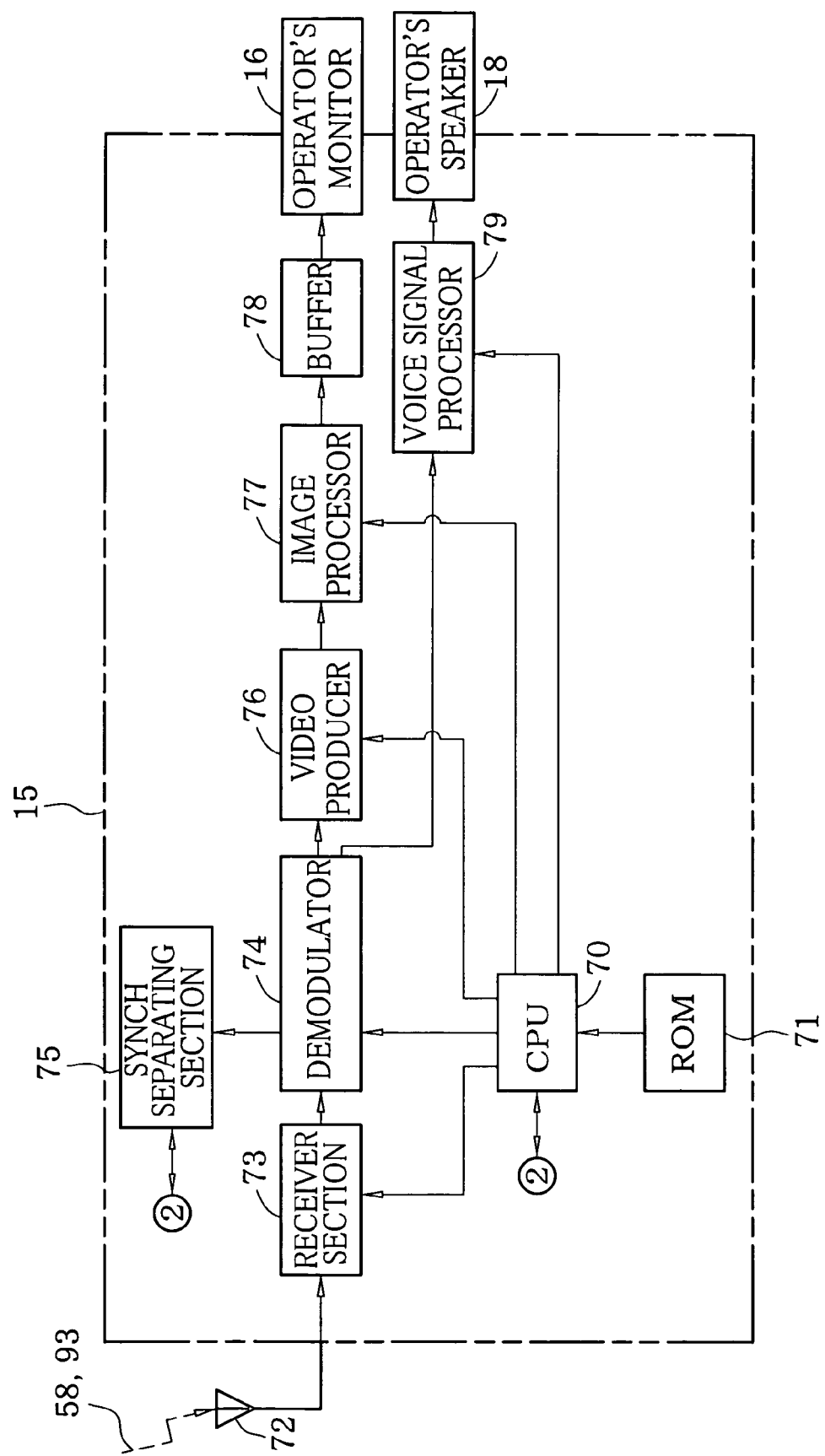

DIAGNOSTIC SYSTEM USING ENDOSCOPE

FIELD OF THE INVENTION

The present invention relates to a diagnostic system using at least an electronic endoscope, wherein an operator of the endoscope is allowed to make a diagnosis in an examination room, while getting instructions and assistances from an instructor staying in a remote room.

BACKGROUND OF THE INVENTION

Medical diagnoses utilizing an electronic endoscope have widely been practiced in the medical field these days. The electronic endoscope has an imaging device like a CCD, which is built in an end of an elongated probing portion that is introduced into a body cavity, so that the CCD takes an image signal from an internal body site. The image signal is processed in a processor, to display an image of the internal body site, called an endoscopic image, on a monitor. For the purpose of making examinations and diagnoses on many patients at the same time, it is usual to install a number of electronic endoscopes and the processors in the same hospital. For example, an examination room is partitioned into a number of compartments, and a pair of electronic endoscope and processor is installed in each compartment.

Meanwhile, in order to support trainees and those doctors who are unskilled at using the electronic endoscope for diagnosis, an operation support system has been suggested for example in Japanese Laid-open Patent Applications Nos. 2000-271147 and 2005-111080, wherein an instruction room is provided for a doctor skilled in the endoscopic diagnosis to monitor endoscopic images obtained through an electronic endoscope that is operated by an operator in a remote examination room, so that the skilled doctor may give proper instructions to the operator in a real time fashion.

In the above-mentioned prior arts, the instruction room and the examination room are interconnected through a communication line, like ISDN, so as to communicate data of the endoscopic images and the instructions through the communication line. However, wiring of the communication line is cumbersome especially where there are a number of examination rooms or booths for the endoscopic examination.

SUMMARY OF THE INVENTION

In view of the foregoing, a primary object of the present invention is to provide a diagnostic system using at least an endoscope, which does not need cumbersome wiring between the examination room and the instruction room, but communicates data through radio communication, to make it easy to install the diagnostic system.

To achieve the above and other objects in a diagnostic system comprising an operator's diagnostic unit installed in an examination room, and an instructor's diagnostic unit installed in an instructor room that is remote from the examination room, wherein the operator's diagnostic unit and the instructor's diagnostic unit communicate with each other so that an operator in the examination room may make a diagnosis while getting instructions from an instructor staying in the instructor room, the operator's diagnostic unit comprises an inquiry data input device for inputting inquiry data; an electronic endoscope which comprises an imaging device for obtaining an image signal from a site to observe inside a body cavity, a device for digitalizing the image signal to be a picture signal, a modulator for producing a first radio frequency signal by subjecting the picture signal to quadrature modulation and superimposing the inquiry data on the modulated picture signal while shifting the phase of the inquiry data, and a sender for sending the first radio frequency signal as a first electric wave; an operator's processor which comprises a receiver for receiving electric waves, a demodulator for demodulating the first radio frequency signal into the original picture signal and the inquiry data when the first electric wave is received from the electronic endoscope, and for deriving instruction data from a second radio frequency signal that is received as a second electric wave from the instructor's diagnostic unit, and a signal processing device for producing an endoscopic image from the picture signal; a monitor for displaying the endoscopic image; and a data output device for outputting the instruction data received from the instructor's diagnostic unit.

On the other hand, the instructor's diagnostic unit comprises an instruction data input device for inputting the instruction data; an instructor's processor which comprises a receiver for receiving the first electric wave from the operator's diagnostic unit, a demodulator for demodulating the first radio frequency signal into the original picture signal and the inquiry data, a signal processing device for producing the endoscopic image from the picture signal, a modulator for modulating the instruction data into the second radio frequency signal, and a sender for sending the second radio frequency signal as the second electric wave to the operator's diagnostic unit; a monitor for displaying the endoscopic image; and a data output device for outputting the inquiry data received from the operator's diagnostic unit.

Preferably, the operator's diagnostic unit and the instructor's diagnostic unit send and receive the inquiry data and the instruction data according to a half-duplex communication method.

The inquiry data and the instruction data include at least one of voice signals, character signals and set-up data for controlling operations of the diagnostic system.

According to a preferred embodiment, the diagnostic system comprises a plurality of the operator's diagnostic units, wherein an individual channel of a frequency band for sending and receiving the electric waves is allocated to each of the operator's diagnostic units, whereas the instructor's diagnostic unit is provided with a switching device for switching between the channels to select one from among the operator's diagnostic units.

Because there is no need for cumbersome wiring between the examination room and the instruction room, installation of the diagnostic system of the present invention is very easy.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 5 is a block diagram illustrating an internal structure of an operator's processor of the system;

DESCRIPTION OF THE PREFERRED EMBODIMENTS

Figure 1:
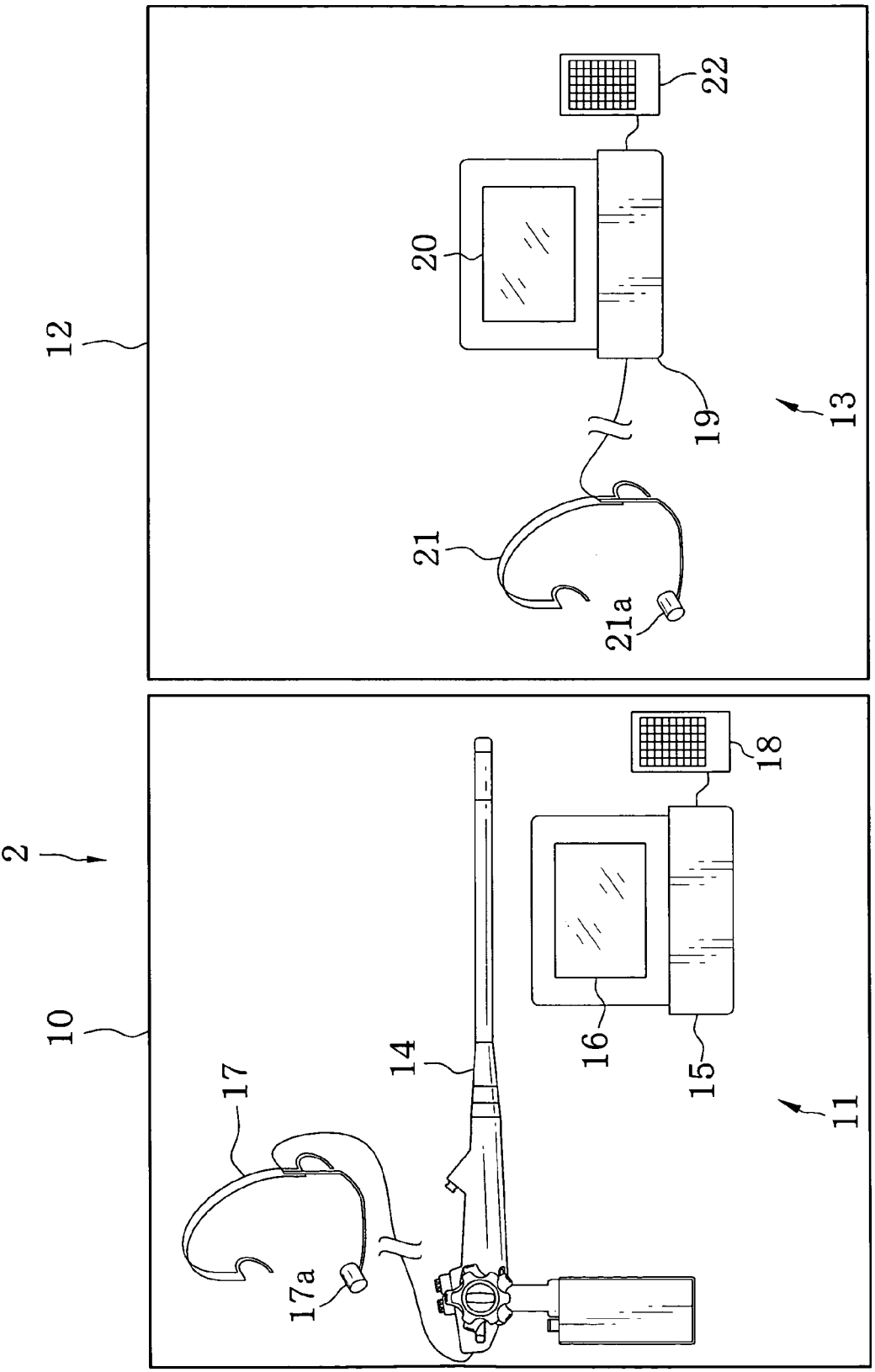
FIG. 1 is a schematic diagram illustrating a diagnostic system using an electronic endoscope, according to an embodiment of the present invention.

FIG. 1 shows a diagnostic system 2 which consists of an operator's diagnostic unit 11 that is installed in an examination room 10 where an operator makes a diagnosis on a patient using an electronic endoscope 14, and an instructor's diagnostic unit 13 that is installed in an instructor room 12 where an instructor gives directions to the operator for the endoscopic diagnoses.

The operator's diagnostic unit 11 consists of the electronic endoscope 14, an operator's processor 15 for producing endoscopic images, an operator's monitor 16 for displaying the endoscopic images, an operator's headset 17 provided with a microphone 17a for inputting voice of the operator, and an operator's speaker 18 for outputting voice of the instructor.

On the other hand, the instructor's diagnostic unit 13 consists of an instructor's processor 19 for producing endoscopic images, an instructor's monitor 20 for displaying the endoscopic images, an instructor's headset 21 provided with a microphone 21a for inputting voice of the instructor, and an instructor's speaker 22 for outputting voice of the operator.

Figure 2:
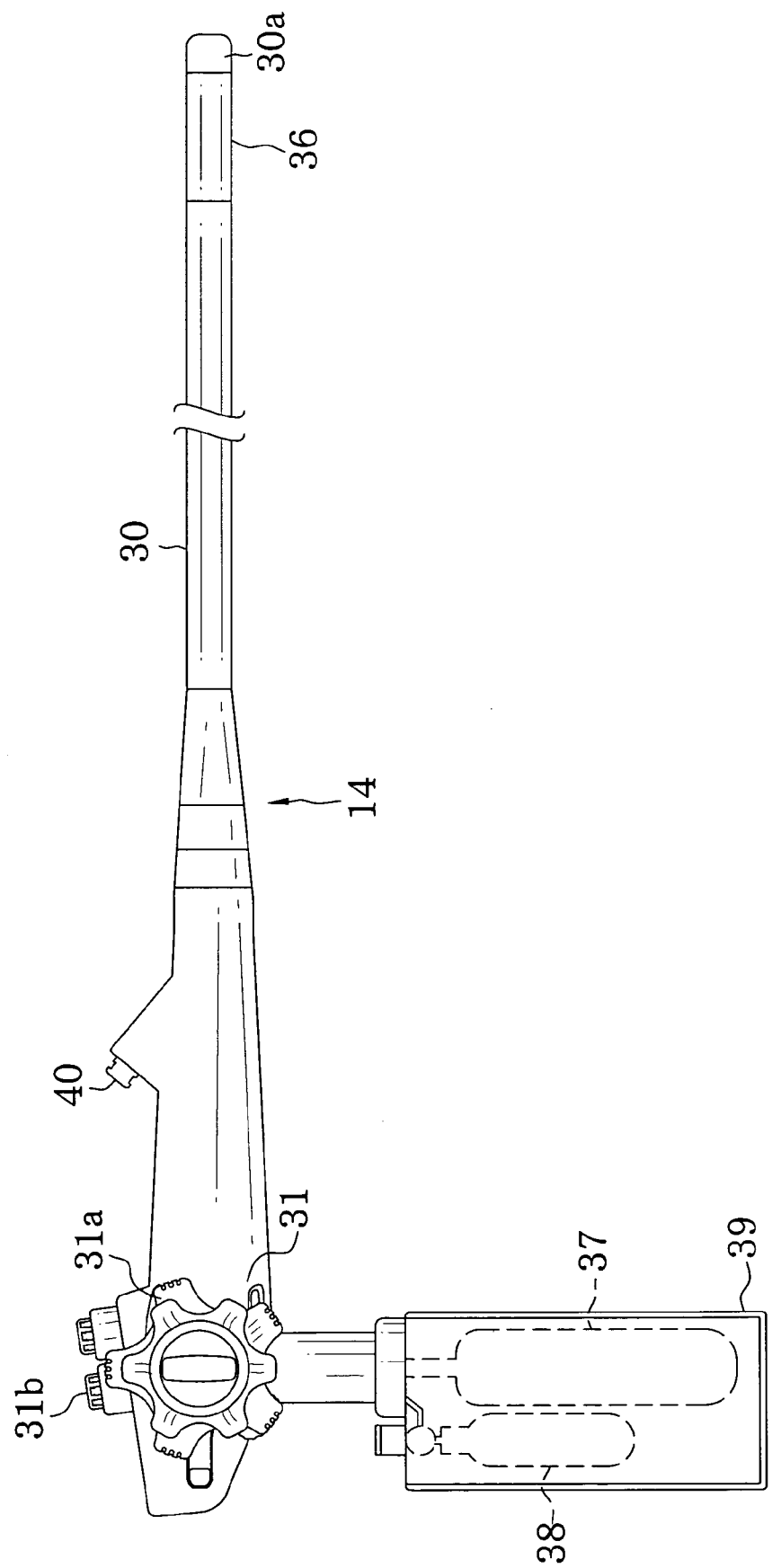
FIG. 2 is a schematic diagram illustrating the electronic endoscope of the system.

In FIG. 2, the electronic endoscope 14 is provided with a probing portion 30 that is introduced into a body cavity, and a control section 31 that is joined to a base end of the probing portion 30. Built in a probe tip 30a, which is joined to a distal end of the probing portion 30, are an objective lens 32 for forming an optical image of an internal body part to be observed, a CCD 33 as an imaging device for capturing the optical image of the internal body part, an illuminative lens 34, and an LED light source 35 for illuminating the body cavity, as shown in FIG. 3.

Behind the probe tip 30a is provided a curving section 36 consisting of a number of linked curving segments. By operating an angle knob 31a on the control section 31, a number of wires, which are not shown but extend in the probing portion 30, are pulled and pushed to curve the curving section 36 appropriately, thereby to direct the probe tip 30a to an aimed point inside the body cavity.

A cartridge 39, in which a water tank 37 containing water and an air tank 38 containing air are built, is detachably attached to a position below the control section 31. In cooperation with an action on a watering/airing button 31b of the control section 31, the water contained in the water tank 37 and the air contained in the air tank 38 are fed through a water pipe and an air pipe and ejected from a wash nozzle toward the objective lens 32, though the water pipe and the air pipe are not shown but disposed in the electronic endoscope 14, and the wash nozzle is not shown but formed through the probe tip 30a. Thereby, dirt on the surface of the objective lens 32 is washed away, and the air is sent to the body cavity. The cartridge 39 is so positioned that the wrist of the operator is held on the cartridge 39 to stabilize the electronic endoscope 14 on operating it. Designated by 40 is an inlet for inserting a treatment tool.

Figure 3:
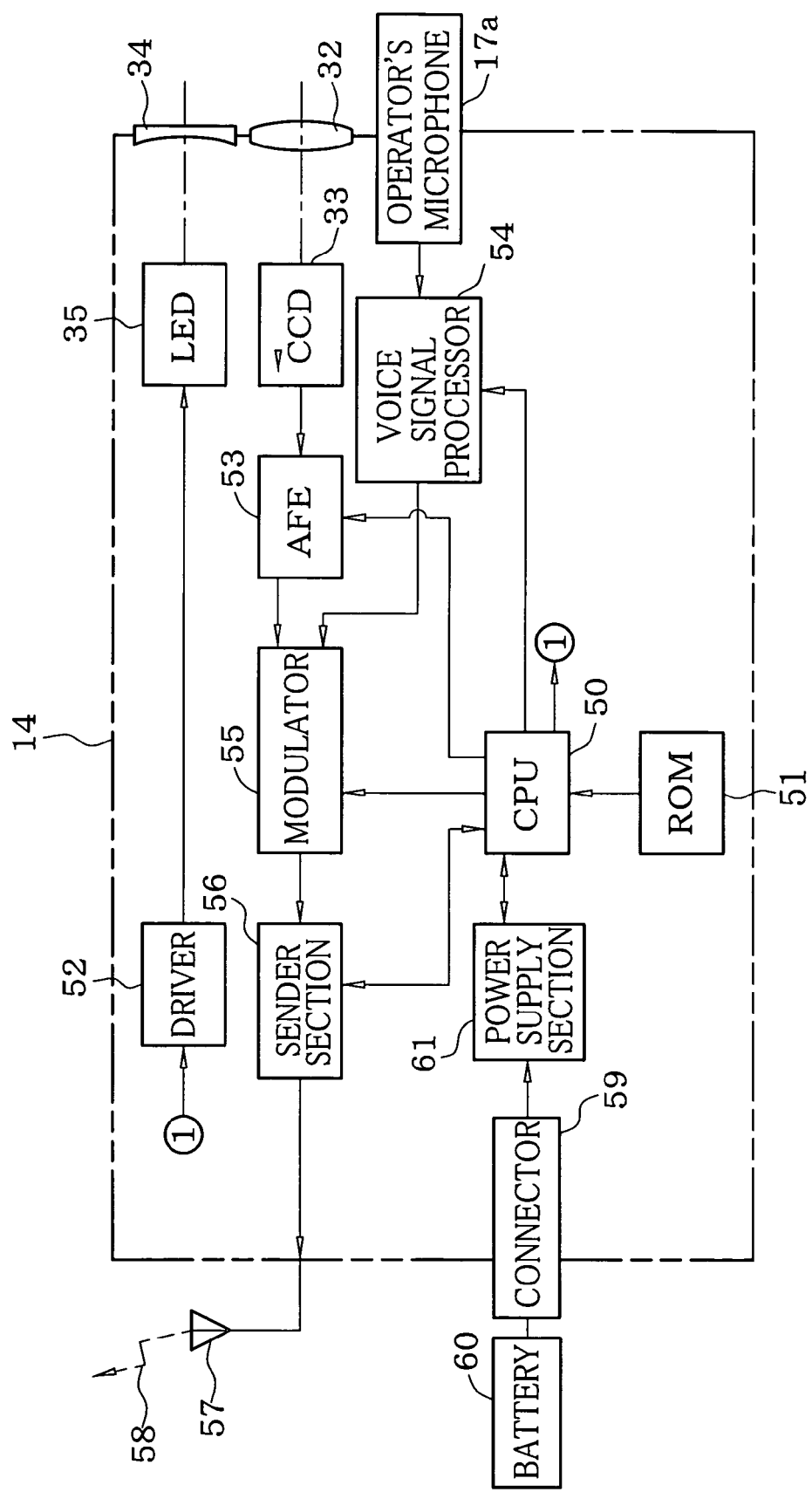
FIG. 3 is a block diagram illustrating an internal structure of the electronic endoscope.

Referring to FIG. 3, the overall operation of the electronic endoscope 14 is under the control of a CPU 50. A ROM 51 storing various programs and data for controlling the operation of the electronic endoscope 14 is connected to the CPU 50. The CPU 50 reads out necessary program and data from the ROM 51, to control the operation of the electronic endoscope 14 based on the read program and data.

A driver 52 is connected to the LED 35. The driver 52 turns the LED 35 on and off under the control of the CPU 50. The light emitted from the LED 35 is projected through the illuminative lens 34 onto the internal body part to observe. Note that the LED 35 is not necessarily located in the probe tip 30a, but may be located in an intermediate portion inside the control section 31. In that case, the light from the LED 35 is guided through a light guide to the probe tip 30a.

An optical image of the internal body part is formed through the objective lens 32 on an imaging surface of the CCD 33, so the CCD 33 outputs from individual pixels analog image signals corresponding to the optical image. The analog image signals are fed to an AFE (analog front end) circuit 53, where the analog image signals are subjected to correlated-double-sampling, and are amplified and converted into a digital picture signal.

To the operator's microphone 17a is connected a voice signal processor 54, so the operator's voice input through the operator's microphone 17a is processed by the voice signal processor 54 for analog-to-digital conversion, noise reduction and the like, to be output as a digital voice signal.

Figure 4:
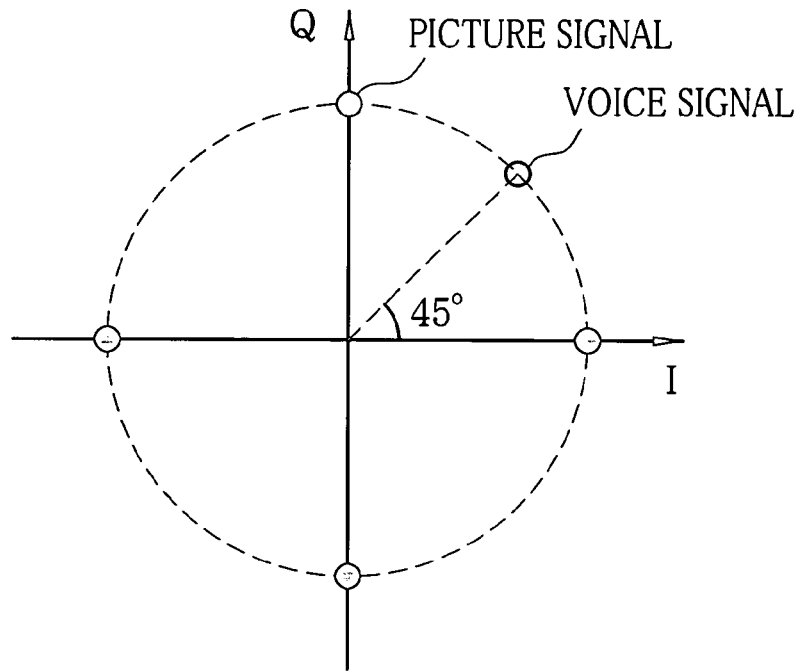
FIG. 4 is an explanatory diagram illustrating a phasor structure of a radio frequency signal produced from the electronic endoscope.

As illustrated in FIG. 4, a modulator 55 produces a radio frequency (RF) signal by subjecting the digital picture signal, which is output from the AFE circuit 53, to digital quadrature modulation of quadraphase-shift keying (QPSK), as implied by four black points in FIG. 4, and superimposing the digital voice signal, which is output from the voice signal processor 54, on the modulated picture signal, while shifting the phase of the voice signal by 45°, as implied by a blank point in FIG. 4.

Referring back to FIG. 3, a sender section 56 sends the RF signal, which is produced from the modulator 55, to the operator's processor 15 and the instructor's processor 19, as an electric wave 58 from an antenna 57.

A connector 59 is connected to batteries 60. The electric power from the batteries 60 is supplied through a power supply section 62 to the respective components of the electronic endoscope 14 under the control of the CPU 50. Although it is omitted from the drawings, a battery chamber for loading the batteries 60 is formed behind the control section 31, and the connector 59 is located inside the battery chamber. Also a not-shown connector for the operator's headset 17 is located inside the battery chamber.

FIG. 4 shows the structure of the operator's processor 15, wherein a CPU 70 controls overall operations of the operator's processor 15. The CPU 70 is connected to a ROM 71 that stores various programs and data for controlling the operations of the operator's processor 15. The CPU 70 reads out necessary ones of these programs and data from the ROM 71, to control the operation of the operator's processor 15 based on the read program and data.

An antenna 72 receives the electric wave 58 from the electronic endoscope 14 and an electric wave 93 from the instructor's processor 19. As set forth in detail later with reference to FIG. 6, the electric wave 93 represents a radio frequency signal that is obtained by modulating a voice signal of the instructor's voice in the instructor's processor 19. The electric waves 58 and 93 received on the antenna 72, i.e. the radio frequency signals, are amplified at a receiver section 73. A demodulator 74 demodulates the RF signal into the original picture signal before being modulated in the electronic endoscope 14, for example, by subjecting the radio frequency signal to digital quadrature detection. The demodulator 74 also demodulates the radio frequency signal received as the electric wave 93 into the original voice signal.

Under the control of the CPU 70, a synch separating section 75 carries out amplitude separation to separate a synchronizing signal from the picture signal as an output of the demodulator 74. Thereafter, the synch separating section 75 carries out frequency separation for separating the horizontal synchronizing signal and the vertical synchronizing signal. A video signal producer 76 produces a digital video signal from the picture signal. An image processor 77 treats the video signal, as produced from the video signal producer 76, with various kinds of image-processing, such as masking and character data attaching. A buffer 78 temporarily stores the video signal as processed in the image processor 77, till the video signal is used for displaying an endoscopic image on the operator's monitor 16.

The voice signal processor 79 processes the voice signal of the instructor's voice, which is output from the demodulator 74, for noise reduction, digital-to-analog conversion and the like, to output the processed voice signal to the operator's speaker 18.

Figure 6:
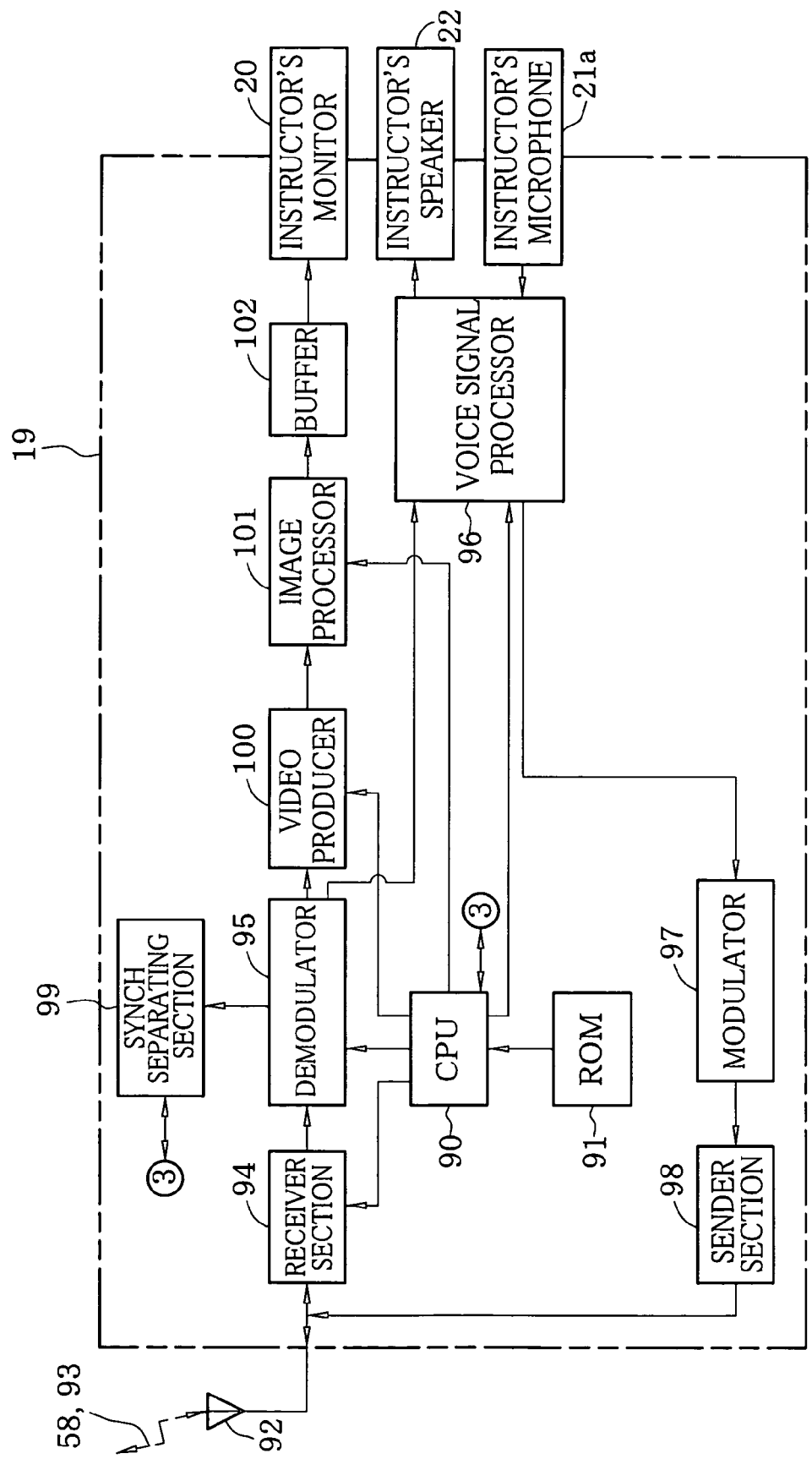
FIG. 6 is a block diagram illustrating an internal structure of an instructor's processor of the system.

FIG. 6 shows the structure of the instructor's processor 19, wherein a CPU 90 controls overall operations of the instructor's processor 19. The CPU 90 is connected to a ROM 91 that stores various programs and data for controlling the operations of the instructor's processor 19. The CPU 90 reads out necessary ones of these programs and data from the ROM 91, and controls the operation of the instructor's processor 19 based on the read program and data.

An antenna 92 is served to receive the electric wave 58 from the electronic endoscope 14, and send the electric wave 93 to the operator's processor 15. The electric wave 58 from the electronic endoscope 14 as received on the antenna 92, i.e. the radio frequency signal, is amplified at a receiver section 94. A demodulator 95 demodulates the radio frequency signal into the original picture signal and the original voice signal, the ones before being modulated in the electronic endoscope 14, for example, by subjecting the radio frequency signal to digital quadrature detection.

To the instructor's microphone 21a is connected a voice signal processor 96, so the instructor's voice input through the instructor's microphone 21a is processed by the voice signal processor 96 for analog-to-digital conversion, noise reduction and the like, to be output as a digital voice signal. The voice signal processor 96 also process the voice signal of the operator's voice, which is output from the demodulator 95, for noise reduction, digital-to-analog conversion and the like, to output the processed voice signal to the instructor's speaker 22.

Figure 7:
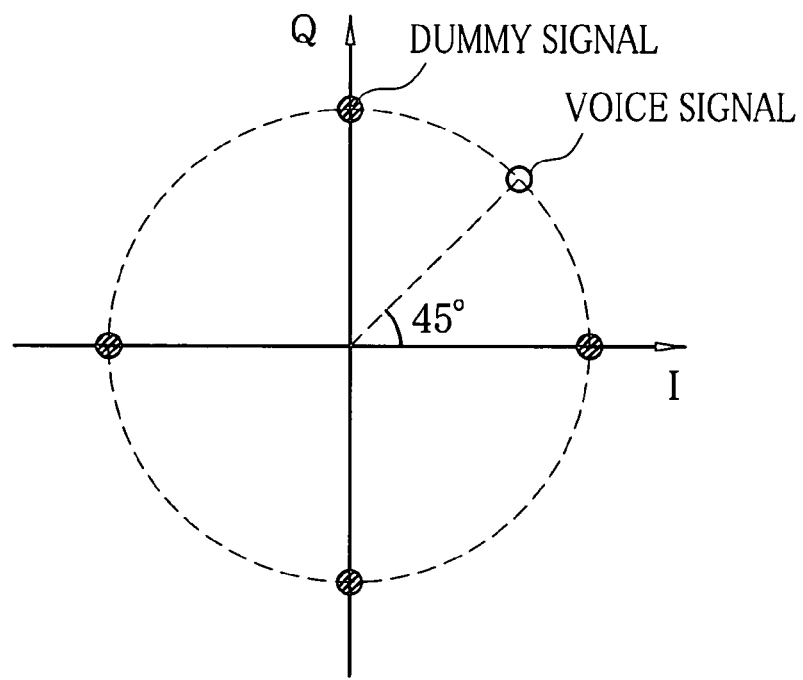
FIG. 7 is an explanatory diagram illustrating a phasor structure of a radio frequency signal produced from the instructor's processor.

A modulator 97 of the instructor's processor 19 produces the radio frequency signal that is to be sent as the electric wave 93. Specifically, as implied by four hatched points in FIG. 7, the modulator 97 substitutes a dummy signal for the modulated picture signal that is modulated in the modulator 55 of the electronic endoscope 14, and then superimposes the digital voice signal as an output of the voice signal processor 95 on the dummy signal, while shifting the phase of the voice signal by 45°, as implied by a blank point in FIG. 7.

Referring back to FIG. 6, a sender section 98 sends the radio frequency signal, which is output from the modulator 97, as the electric wave 93 from the antenna 92 to the operator's processor 15. A synch separating section 99 carries out amplitude separation to separate a synchronizing signal from the picture signal and, thereafter, separates the horizontal synchronizing signal and the vertical synchronizing signal through frequency separation. A video signal producer 100 produces a digital video signal from the picture signal. An image processor 101 treats the video signal with various kinds of image-processing, such as masking and character data attaching. The processed video signal is temporarily stored in a buffer 102.

The operator's diagnostic unit 11 and the instructor's diagnostic unit 13 send and receive the voice signal on the electric waves 58 and 93 according to a half-duplex communication method. Concretely, even when the electric wave 93 from the instructor's processor 19, which carries the instructor's voice, is received on the receiver section 73, if the radio frequency signal received as the electric wave 58 is composed of the picture signal and the voice signal, that is, while the operator is inputting some question to the instructor vocally through the operator's microphone 17a, the CPU 70 of the operator's processor 15 controls the voice signal processor 79 so as not to output the instructor's voice from the operator's speaker 18. The CPU 70 may alternatively control the receiver section 73 of the operator's processor 15 so as to refuse the electric wave 93 from the instructor's processor 19, when the electric wave 58 received on the receiver section 73 carries the voice signal of the operator's voice.

In the instructor's processor 19, on the other hand, while the electric wave 93 is being sent from the sender section 98, that is, while the instructor is inputting an instruction to the operator vocally through the instructor's microphone 21a, the CPU 90 controls the voice signal processor 96 so as not to output the operator's voice from the instructor's speaker 22 even when the electric wave 58 carrying the voice signal of the operator's voice is received on the receiver section 94. Thus, the half-duplex communication prevents interference or confusion between the operator's voice and the instructor's voice.

To observe a body cavity with the diagnostic system 2, first the LED light source 35 is turned on, and the probing portion 30 is introduced into the body cavity, to take endoscopic images through the CCD 33 while illuminating the inside of the body cavity. The taken endoscopic images are observable on the monitor 16.

Concretely, an optical image of a body part inside the body cavity is formed on the imaging surface of the CCD 33 through the objective lens 32, so the CCD 33 outputs image signals corresponding to the optical image. The analog image signals are subjected to correlated-double-sampling, and are amplified and converted into a digital picture signal at the AFE 53.

The digital picture signal, as output from the AFE 53, is subjected to digital quadrature modulation in the modulator 55, thereby to produce the radio frequency signal. The radio frequency signal is amplified at the sender section 56, and then sent as the electric wave 58 from the antenna 57.

On the other hand, the electric wave 58 sent from the antenna 57 of the electronic endoscope 14 is received as the radio frequency signal on the antenna 72 of the processor 15, and is amplified in the receiver section 73. The demodulator 74 subjects the amplified radio frequency signal to digital quadrature detection, to demodulate the radio frequency signal into the original picture signal before being modulated in the electronic endoscope 14.

The picture signal demodulated in the demodulator 74 is subjected to the synch separation processes in the synch separating section 74 under the control of the CPU 70. The video signal producer 76 produces the digital video signal from the picture signal. The video signal is subjected to various kinds of image-processing in the image processor 77. The processed video signal is stored temporarily in the buffer 78, and is displayed as the endoscopic images on the monitor 16. In the same way as the operator's processor 15, the instructor's processor 19 produces the endoscopic image from the electric wave 58 as sent from the electronic endoscope 14, and displays the produced endoscopic image on the instructor's monitor 20. In this way, the electronic endoscope 14, the operator's processor 15 and the instructor's processor 19 communicate the picture signal to each other by way of the electric wave 58.

Next will be described a sequence of operation performed when the operator inquires for an instructor's direction by inputting the voice through the operator's microphone 17a.

The operator's voice input through the operator's microphone 17a is subjected to various processing in the voice signal processor 54, to be converted into a digital voice signal. The digitalized voice signal is superimposed on a picture signal that has gone through the digital quadrature modulation in the modulator 55, while shifting the phase of the voice signal. A radio frequency signal composed of the voice signal and the picture signal in this way is sent the sender section 56 to the antenna 57, to be sent as the electric wave 58 to the operator's processor 15 and the instructor's processor 19.

In the operator's processor 15, an endoscopic image is produced from the electric wave 58 in the way as described above. In the instructor's processor 19, on the other hand, when the electric wave 58 is received on the antenna 92, the radio frequency signal represented by the electric wave 58 is fed through the receiver section 94 to the demodulator 95, so the radio frequency signal is demodulated into the original picture signal and the original voice signal.

The demodulated picture signal is processed in the same way as in the operator's processor 15, to display an endoscopic image on the instructor's monitor 20. Simultaneously, the demodulated voice signal is processed in the voice signal processor 96, to output the operator's voice through the instructor's speaker 22. Thus, the operator can make inquiries for instructor's assistances through the operator's microphone 17a, while the instructor can hear the inquiries from the operator through the instructor's speaker 22.

On the other hand, when the instructor inputs an instruction about an endoscopic diagnosis vocally through the instructor's microphone 21a, the instructor's voice input through the instructor's microphone 21a is subjected to various processing in the voice signal processor 96, to be converted into a digital voice signal. The digitalized voice signal is superimposed on the dummy signal that has gone through the digital quadrature modulation in the modulator 97, while shifting the phase of the voice signal. A radio frequency signal composed of the voice signal and the dummy signal in this way is sent through the sender section 98 to the antenna 92, to be sent as the electric wave 93 to the operator's processor 15.

In the operator's processor 15, when the electric wave 93 is received on the antenna 72, the radio frequency signal represented by the electric wave 93 is fed through the receiver section 73 to the demodulator 74, so the radio frequency signal is demodulated into the original dummy signal and the original voice signal.

The demodulated voice signal is processed in the voice signal processor 79, to output the instructor's voice through the operator's speaker 18. Thus, the instructor can give instructions to the operator through the instructor's microphone 21a, while the operator can hear the instructions of the instructor through the operator's microphone 17a.

However, even when the electric wave 93 from the instructor's processor 19, which carries the instructor's voice, is received on the receiver section 73, if the radio frequency signal received as the electric wave 58 on the receiver section 73 is composed of the picture signal and the voice signal, the CPU 70 of the operator's processor 15 controls the voice signal processor 79 so as not to output the instructor's voice from the operator's speaker 18. Alternatively, the CPU 70 controls the receiver section 73 of the operator's processor 15 so as to refuse the electric wave 93 from the instructor's processor 19, when the electric wave 58 received on the receiver section 73 carries the voice signal of the operator's voice.

Also in the instructor's processor 19, if the electric wave 93 is to be sent from the sender section 98, the CPU 90 controls the voice signal processor 96 so as not to output the operator's voice from the instructor's speaker 22 even when the electric wave 58 carrying the voice signal of the operator's voice is received on the receiver section 94. In this way, the operator's diagnostic unit 11 and the instructor's diagnostic unit 13 send and receive the voice signals on the electric waves 58 and 93 according to the half-duplex communication method.

Figure 8:
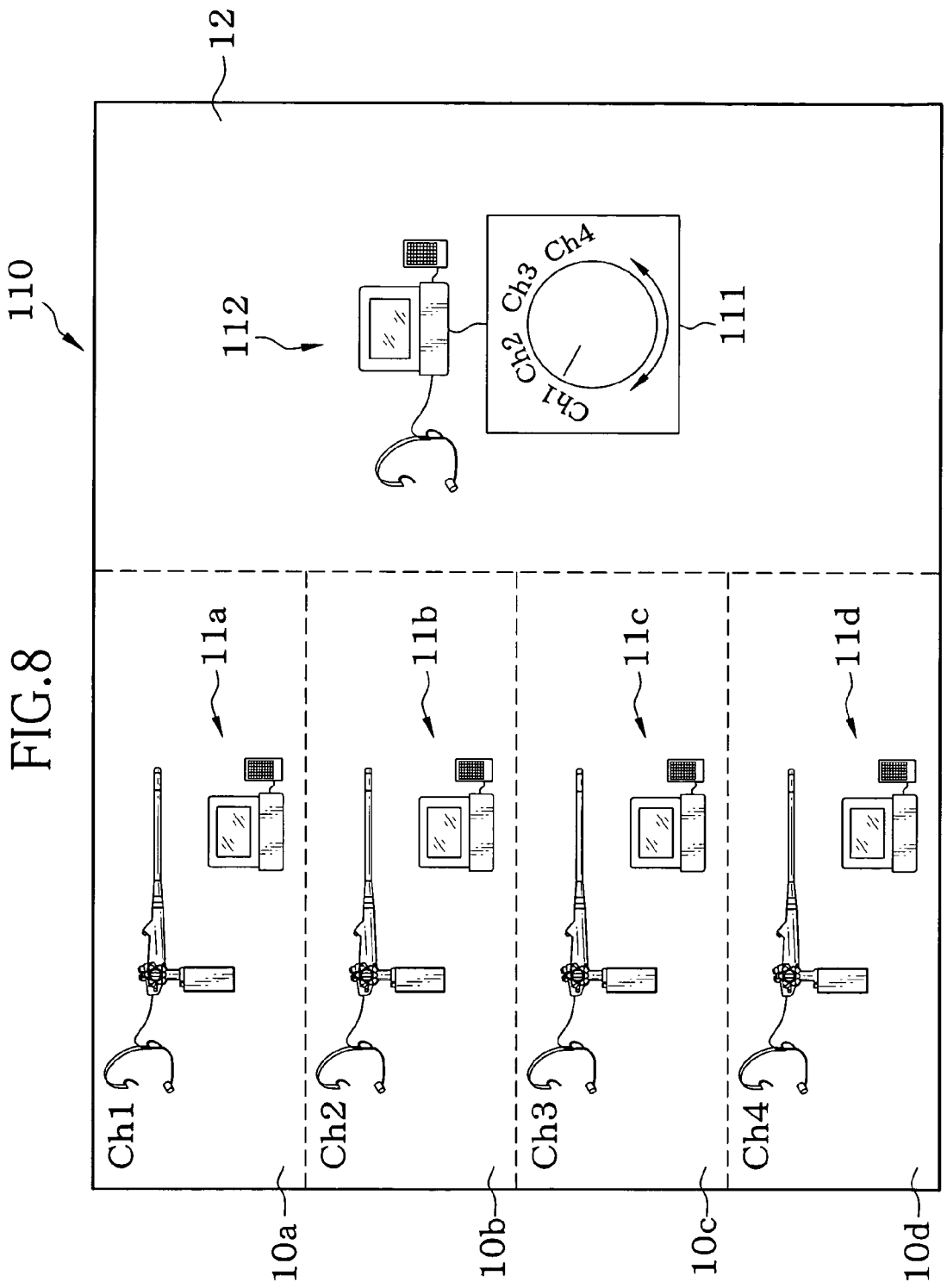
FIG. 8 is a schematic diagram illustrating a diagnostic system including a number of electronic endoscopes, according to another embodiment of the present invention.

Although the present invention has been described with respect to the embodiment where only one operator's diagnostic unit 11 is installed in the diagnostic system 2, the present invention is applicable to a case where a number of diagnostic units 11a, 11b, 11c and lid for operators are installed in examination rooms 10a, 10b, 10c and 10d, as shown in FIG. 8.

In a diagnostic system 110 shown in FIG. 8, individual channels Ch1, Ch2, Ch3 and Ch4 of frequency bands for sending and receiving the electric waves 58 and 93 are allocated to the operator's diagnostic units 11a to 11d. A diagnostic unit 112 for an instructor, which is installed in an instructor room 12, is provided with a switching dial 111 for switching between the channels Ch1 to Ch4. In the instructor's diagnostic unit 112, an endoscopic image from one of the operator's diagnostic units 11a to 11d, which corresponds to the channel selected by the switching dial 111, is displayed on an instructor's monitor 20. Communication between the instructor and the operator is possible only through the selected channel.

It is preferable for the case using a number of operator's diagnostic units, like the diagnostic system 110, that the instructor's diagnostic unit 112 and each individual operator's diagnostic unit 11a, 11b, 11c or 11d send and receive inquiry data and instruction data through the same channel by shifting the phase from each other according to a half-duplex communication method. Thereby, each of the operator's diagnostic units 11a, 11b, 11c and 11d uses a single channel for sending and receiving the signals. So the diagnostic system 110 can hold as much operator's diagnostic units as possible for available channels.

Although communication between the instructor and the operator is done by sending voice signals in the above-described embodiments, it is possible to provide the respective diagnostic units 11 and 13 with character input devices like keyboards, so that the inquiries and the instructions may be sent as character signals, to be displayed on the monitors 16 and 20. It is also possible to send set-up data for controlling operations of designated components, such as processing parameters for the AFE 53 and the image processor 77, in place of the voice signal or the character signals.

Thus, the present invention is not to be limited to the illustrated embodiments. On the contrary, various modifications will be possible without departing from the scope of claims appended hereto.

What is claimed is:

1. A diagnostic system comprising an operator's diagnostic unit installed in an examination room, and an instructor's diagnostic unit installed in an instructor room that is remote from the examination room, said operator's diagnostic unit and said instructor's diagnostic unit communicating with each other so that an operator in the examination room may make a diagnosis while getting instructions from an instructor staying in the instructor room, wherein said operator's diagnostic unit comprises:

an inquiry data input device for inputting inquiry data;

an electronic endoscope which comprises an imaging device for obtaining an image signal from a site to observe inside a body cavity, a device for digitalizing the image signal to be a picture signal, a modulator for producing a first radio frequency signal by subjecting the picture signal to quadrature modulation and superimposing the inquiry data on the modulated picture signal while shifting the phase of the inquiry data, and a sender for sending the first radio frequency signal as a first electric wave;

an operator's processor which comprises a receiver for receiving electric waves, a demodulator for demodulating the first radio frequency signal into the original picture signal and the inquiry data when the first electric wave is received from said electronic endoscope, and for deriving instruction data from a second radio frequency signal that is received as a second electric wave from said instructor's diagnostic unit, and a signal processing device for producing an endoscopic image from the picture signal;

a monitor for displaying the endoscopic image; and a data output device for outputting the instruction data received from said instructor's diagnostic unit; and wherein said instructor's diagnostic unit comprises:

an instruction data input device for inputting the instruction data;

an instructor's processor which comprises a receiver for receiving the first electric wave from said operator's diagnostic unit, a demodulator for demodulating the first radio frequency signal into the original picture signal and the inquiry data, a signal processing device for producing the endoscopic image from the picture signal, a modulator for modulating the instruction data into the second radio frequency signal, and a sender for sending the second radio frequency signal as the second electric wave to said operator's diagnostic unit;

a monitor for displaying the endoscopic image; and a data output device for outputting the inquiry data received from said operator's diagnostic unit.

2. A diagnostic system as claimed in claim 1, wherein said operator's diagnostic unit and said instructor's diagnostic unit send and receive the inquiry data and the instruction data according to a half-duplex communication method.

3. A diagnostic system as claimed in claim 2, wherein said data output device of said operator's diagnostic unit is controlled so as not to output the instruction data while the operator is inputting the inquiry data through said inquiry data input device, whereas said data output device of said instructor's diagnostic unit is controlled so as not to output the inquiry data while the instructor is inputting the instruction data through said instruction data input device.

4. A diagnostic system as claimed in claim 1, wherein the inquiry data and the instruction data include at least one of voice signals, character signals and set-up data for controlling operations of said diagnostic system.

5. A diagnostic system as claimed in claim 1, comprising a plurality of said operator's diagnostic units, wherein an individual channel of a frequency band for sending and receiving the electric waves is allocated to each of said operator's diagnostic units, whereas said instructor's diagnostic unit is provided with a switching device for switching between the channels to select one from among said operator's diagnostic units.

6. A diagnostic system as claimed in claim 1, wherein said modulator of said electronic endoscope modulates the picture signal according to a quadraphase-shift keying method, and superimposes the inquiry data as on the modulated picture signal while shifting the phase of the inquiry data by 45°, whereas said modulator of said instructor's processor modulates a dummy signal in the same way as the picture signal, and superimposes the instruction data on the modulated dummy signal, while shifting the phase of the instruction data by 45°.

* * * * *